United States Patent [19]

Murzakov et al.

[11] Patent Number: 5,496,723
[45] Date of Patent: Mar. 5, 1996

[54] STRAINS OF ACINETOBACTER SPECIES (BICOCCUM), ARTHROBACTER SPECIES, AND RHODOCOCCUS SPECIES, AND A METHOD FOR BIOLOGICAL PURIFICATION FROM OIL SPILLS AND POLLUTIONS, USING SAID STRAINS

[75] Inventors: Boris G. Murzakov, Novoe shosse, d.91, kv.15, 142712 Moskovskaya obl., Gorki Leninskie; Alexandra I. Zaikina; Rufina A. Rogacheva, both of Moscow; Elena V. Semenova, Moskovskaya, all of Russian Federation

[73] Assignee: Boris G. Murzakov, Moskovskaya, Russian Federation

[21] Appl. No.: 313,167

[22] PCT Filed: Feb. 15, 1993

[86] PCT No.: PCT/RU93/00045

§ 371 Date: Oct. 7, 1994

§ 102(e) Date: Oct. 7, 1994

[87] PCT Pub. No.: WO94/18132

PCT Pub. Date: Aug. 18, 1994

[51] Int. Cl.$^6$ .................................... C12N 1/12
[52] U.S. Cl. .................. 435/252.1; 435/281; 435/822
[58] Field of Search .................. 435/252.1, 281, 435/822

[56] References Cited

U.S. PATENT DOCUMENTS

| | | |
|---|---|---|
| 3,069,325 | 12/1962 | Hitzman . |
| 3,871,957 | 3/1975 | Mohan et al. ............ 435/281 |
| 4,415,661 | 11/1983 | Thirumalachar .......... 435/281 |
| 4,415,662 | 11/1983 | Thirumalachar .......... 435/281 |
| 4,605,502 | 8/1986 | Hata . |
| 4,808,535 | 2/1989 | Isbister . |

FOREIGN PATENT DOCUMENTS

| | | |
|---|---|---|
| 0141784 | 5/1985 | European Pat. Off. . |
| 612958 | 6/1978 | U.S.S.R. . |
| 823314 | 4/1981 | U.S.S.R. . |
| 1428809 | 10/1988 | U.S.S.R. . |

OTHER PUBLICATIONS

Biotech Abstract 83–07460 Neufeld et al J. Ferment. Technol (1983) vol. 61, No. 3 pp. 315–321.

*Primary Examiner*—Herbert J. Lilling
*Attorney, Agent, or Firm*—Collard & Roe

[57] ABSTRACT

The strains of Acinetobacter species (bicoccus) B-6445, Arthrobacter species S-1212, and Rhodococcus species S-1213 were deposited on Jan. 1, 1993 in the All-Union collection at the All-Union research institute for genetics and selection of microorganisms.

A method for biological purification from oil pollutions and spills incorporates introduction of a bacterial culture into the pollution or spill, used as the bacterial culture being made of the strains mentioned before, taken either individually or in any combination with one another, the weight ratio between the bacterial culture and the oil pollution being $1:10-10^5$, respectively.

5 Claims, No Drawings

STRAINS OF ACINETOBACTER SPECIES (BICOCCUM), ARTHROBACTER SPECIES, AND RHODOCOCCUS SPECIES, AND A METHOD FOR BIOLOGICAL PURIFICATION FROM OIL SPILLS AND POLLUTIONS, USING SAID STRAINS

TECHNICAL FIELD

The present invention relates in general to microbiology and more specifically to novel strains of Acinetobacter species (bicoccum), Arthrobacter species, and Rhodococcus species and to a method for biological purification from oil spills and pollutions, using said strains.

The strains mentioned before can find widespread application in environmental restoration of ecological conditions in oil-producing areas and areas where oil products are handled, as well as for recultivation of land and clearing of water ponds and basins.

BACKGROUND ART

Ecological violations of the natural environmental conditions caused by oil spillage at the places of its production, storage, transportations, processing, and utilization become still more and more widespread. According to the data of world literature, up to 10 mln tons of oil area annually discharged in seas and oceans the world over only due to wrecks of tankers. Such emergency oil discharges are causative of perishing the living organisms constituting the ecosystem, while restoration of its integrity involves initiation of the hydrocarbon destruction process. Thousands of hectares of fertile soils and pastures are brought out of agricultural use in the oil-producing regions, fishery ponds and pot water supply sources are polluted. Cleaning of tanker tanks after oil handling is also an important problem.

There are encountered a plurality of diverse groups of microorganisms feeding on petroleum hydrocarbons. However, cleaning capacities of said microorganisms as to time and degree of cleaning are quite unsatisfactory, especially in cases of intensive pollution of soil and water.

There are used currently a number of diverse methods and processes for cleaning oil pollutions, a special place among them being occupied by biological treatment methods. Such methods involve use of microorganisms, bacteria, yeast, and fungi.

Known in the present state of the art is the use of the naturally occurring strain of *Pseudomanas putide*-36 in a method for soil cleaning of oil pollutions (SU, A, 1,428, 809). According to the method, purification is performed by introducing the biomass of the bacterial culture of said strain into oil pollution. The bacterial culture is introduced along with a mineral fertilizer, containing nitrogen in the nitrate form. The minimum concentration of the culture inserted is $10^4$ cells per mg per liter with the consumption rate of the aqueous mixture of from 0.5 to 1 l per sq. m.

The method enables soil to be purified of oil pollutions. However, the bacterial culture used is grown on a scarce feeding carbohydrate substrate, which is not an optimum one because the enzymes engaged in its oxidation are other than the oil destructing enzymes. This results in a reduced purification intensity due to adaptation of the culture to the new substrate. In addition, said strain of Pseudomonas putida-36 features hemolytic and gelatinase activity, which prevents the development of the self-cleaning process with the aid of microorganisms.

The degree of purification attainable by said method is but inadequately high. The method has a limited application being suitable only for soil purification. Moreover, use of the nitrate forms of nitrogen involved in this method results in additional contamination of the environment with toxic nitrate-ions.

DISCLOSURE OF THE INVENTION

It is primary and essential object of the invention to provide, by selection and using novel strains, such a biological method for purification from oil pollutions and spills that makes it possible to purify diverse polluted objects with a high intensity and high degree of purification, without affecting the environmental ecological conditions.

The foregoing object is accomplished due to the fact that, according to the invention, disclosed herein are novel strains of Acinetobacter species (bicoccum) B-6445, Arthrobacter species S-1212, and Rhodococcus special S-1213 deposed on Jan. 19, 1993 in the All-Union collection of industrial microorganisms at the All-Union Research Institute for Genetics and Selection of Microorganisms.

The strains proposed herein are in fact the saprophytic naturally occurring strains which possess a strong oxidizing ability with respect to a wide range of hydrocarbons having diverse chemical structure and are featured by good adaptability to natural cenoses.

The aforementioned strains being the sole carbon source, they can assimilate a broad range of hydrocarbons making part of oil, that is, n-alkanes $C_8$–$C_{38}$, cycloalkanes, aromatic hydrocarbons, asphaltenes, mixtures of crude liquid paraffins, resinous substances, petroleum oils, diesel-fuel fractions, mazout, and crude oil (more than 25 crude oil components all in all).

In the course of vital activity of said microorganisms the hydrocarbons utilized by said strains turn into cellular substances (proteins, lipids, nuclei acids, carbohydrates) and carbon dioxide gas, which are then incorporated into a common cycle of turnover of substances in the biosphere. Once the process of purification from oil products has been completed the resultant biomass is introduced, under the action of the regulatory trophic mechanisms, into the cycle of natural microbiocenoses, while an excess amount of the biomass dies off and turns, under the effect of saprophytic microflora, into humus substances of the soil, or into a complete protein-vitamin mass consumed by aquatic fauna.

The strains are nonpathogenic, nontoxic, and have no hemolytic activity.

The proposed strain of Acinetobacter species (bicoccum) B-6446 has been selected from the flow-through activated sludge, is gram-negative, and is featured by the following cultural-morphological and physiological-biochemical characteristics.

Cultural-morphological characteristics

Cells on meat-infusion agar are immobile, appearing as short thick rods measuring 1.2–1.8 1.5–2.4 m in a young culture, and having a coccal shape measuring 1.5 m in a three-day culture. The culture forms no spores. Three-day colonies grown on meta-infusion agar are rounded in shape, with even edges, whitish in color, glossy, of the sour-cream consistency.

Physiological-biochemical characteristics

Obligate aerobe. Chemoorganotroph. Catalase-positive. Oxidase-negative. No demand for vitamins and additional growth factors. Grows in a broad range of the culture medium pH values (3.8–8.5) and temperatures (10°–35° C.) utilizes mineral nitrogen and fixes atmospheric nitrogen.

The proposed strain of Rhodococcus special S-1213 has been selected from the flow-through activated sludge, is gram-positive, and is featured by the following cultural-morphological and physiological-biochemical characteristics.

Cultural-morphological characteristics

Cells on meat-infusion agar are immobile, single, of the short-oval shape and rods variable in shape and size. The cells of a young culture may form chains, those of an old culture may form cocci. Rods are 1.0–1.7 m in size. No spores are formed by the culture.

Three-day colonies grown on meat-infusion agar of the rounded shape with an even edge, colored light-creamish, glossy, uniformly raised.

Physiological-biochemical characteristics

Obligate aerobe. Chemoorganotroph. Catalase-positive, oxidase-negative. No demans for vitamins and additional growth factors. Grows in a broad range of the culture medium pH values (3.0–8.5) and temperatures (10°–43° C.). An optimum temperature is within 25°–30° C. Utilizes mineral nitrogen.

The biomass of the bacterial culture is obtained using the routine technique of cultivation of the strains of Acinetobacter species (bicoccum) B-6445, Arthrobacter species S-1212, and Rhodococcus specias S-1213 on any standard nutrient medium, e.g., on a mineral onek containing the sources of nitrogen, phosphorus, and microelements. Such a culture medium may be, e.g., Höttinger-King's, wherein used as the carbon source may be carbohydrates, organic acids, alcohols, hydrocarbons, paraffins, or crude oil. The bacteria cultivation conditions are also traditional.

The subject matter of the invention is also a method for biological purification from oil pollutions and spills comprising introduction of a bacterial culture into the oil pollutions or spill, wherein, according to the invention, used as the bacterial culture is the strain of Acinetobacter species (bicoccum) B-6445, Arthrobacter species S-1212, and/or Rhodococcus species 1213, the weight ratio between the biomass of the bacterial culture and the oil spill being 1:10–$10^5$, respectively.

As it has been stated before, the proposed strains are featured by a high growth activity on a mineral nutrient medium, wherein used as a sole carbon source are crude oil and oil products. Once the biomass of said bacterial cultures has been introduced into the oil spill, the substrate is being consumed by the bacteria, whereby the oil products are destructed, with the result that the oil spill is eliminated and the polluted area is purified.

The aforementioned weight ratio between the biomass of the bacterial culture and the oil pollution or spill is an optimum one and provides for purification with a high degree of purity (90–100%). When the amount of the biomass of the bacterial culture introduced into the polluted object is below than that specified before, duration of the purification process is much prolonged, whereas a greater amount of the biomass of the bacterial culture used compared to the aforesaid upper limit does not add to the purification efficiency and the cost of purification is increased.

In cases where the object to be purified is free from the salts of nitrogen and phosphorus or said salts are in a small amount, it is recommendable to effect biological purification in the presence of mineral salts of nitrogen and phosphorus.

With a view to intensifying the purification process it is also recommendable to carry out purification in the presence of microelements, namely, iron, zinc, manganes, and/or magnesium. The presence of said elements contributes to oil destruction.

The amount of mineral additives (the sources of nitrogen, phosphorus, potassium, magnesium, and so on) depends on the composition of the object being purified (i.e., soil or water) and is calculated by determining the concentration of said elements in the natural object and estimating their deficit as to the amount necessary for destruction of the oil pollution.

The proposed method for biological purification from oil pollutions makes it possible to purify polluted objects irrespective of the degree of pollution and with a high effectiveness. The degree of purification attainable by the proposed method amounts to 100%. The method is the multipurpose one, being suitable for purifying soils, natural and man-made water basins, industrial sewage, as well as diverse technological equipment. The method is ecologically pure. The biomass of the bacterial culture being introduced requires no use of any additives. Mineral salts used, according to the method, are completely consumed in the course of bacterial metabolism. The bacterial culture biomass itself is incorporated into the natural soil biocenosis, thus improving its agricultural state, or serves as an additional source of plankton feed in cases where water basins are to be purified. Any pollution of ground water is avoided, since the proposed natural bacterial strains are in fact the obligate aerobes which are liable to perish in the absence of oxygen. The present method makes it possible to intensify the process of recultivation of agricultural lands and purification of fishery ponds, that is, to return lands and water basins into regular use in national economy and at the same time to provide environmental sanitation.

The method is also featured by the low consumption of the biomass.

BEST METHOD CARRYING OUT THE INVENTION

The method for biological purification of oil pollutions and spills is technologically simple and is carried into effect as follows.

Depending on its application the thus-obtained biomass of the bacterial culture is used as an aqueous suspension, paste, or powder. Thus, for instance, when purifying water basins, it is expedient to use powdery biomass, while the biomass in the form of a suspension or paste is to be used when purifying soil.

Suspension and paste are as a rule used in areas situated closely to the enterprises producing them. The working life of such a biomass is up to eight months (at a temperature below 15° C.). The dried biomass has a validity period of at least two years; it appears as a finally divided slightly lumpy or clodded powder colored yellowish-gray, storable well in kraft-paper bags in dry places at a temperature below room temperature but above zero.

Whenever mineral additives are to be used they are applied either in a mixture with the biomass or individually as aqueous solution.

The polluted areas of soil, water, containers, and other objects are treated with the aid of diverse technological equipment and machineries, units, fire-fighting trains, helicopters, or aircraft, as well as manually.

The proposed method provides for soil treatment without removing the layers thereof, through in some cases soil is to be loosened (e.g., polluted sand, gravel, or oil-impregnated soil).

Purification of water basins is carried out by applying the biomass of the bacterial culture to the polluted surface by, e.g., spraying.

Containers and vessels are purified by placing a preprepared suspension thereinto, following by stirring.

for better understanding of the present invention given below are some specific examples of its practical application.

A tank 150 cm high and 50 cm in diameter is filled with 200 l of water, containing 4 wt. % of sea-salt, a 5 mm thick crude-oil layer (1 kg) being spread over the water surface. Then 20 kg of the biomass of the bacterial culture of the strain of Rhodococcus species S-1213 in the powdery state is added to the contents of the tank, the weight ratio between biomass and the oil being $1:10^2$. The tank contents are stirred by air bubbling. In two days the content of n-alkanes decreases by 92.4%, that of aromatic hydrocarbons, by 90.1%. A 100% cleaning is completed within seven days.

EXAMPLE 2

A 200 l vessel is polluted at the bottom and on the walls with 3 kg of an oil product (mazout). The vessel is subjected to mechanical washing with water (100 l) which is doped with the strain of Acinetobacter species B-6445 as a suspension having a concentration of 0.1 g of the bone-dry biomass per liter (the weight ratio between the biomass and mazout being $1:10^3$). Added to the vessel are also the following mineral salts (g/l): $NH_4H_2PO_4$, 10; $KH_2PO_4$, 10; and $MgSO_4 \cdot 7H_2O$, 0.7. In two days the content of n-alkanes is reduced by 93.7%, that of aromatic hydrocarbons, by 89.6%. A 100% cleaning is completed in eight days.

EXAMPLE 3

A land area of one hectare polluted with 12.5 t of crude oil (12.5 kg/m$^2$) is subjected to a single treatment with the biomass of the bacterial culture in the form of an aqueous suspension of the strain of Arthrobacter species S-1212 in an amount of 12 kg of the bone-dry biomass (the weight ratio between the biomass and the oil being $1:10^3$). In seven days the following changes are observed visually on the soil surface: the oil surface becomes dull and is perforated with minute pores resulting from carbon dioxide gas evolution, the color changes from black through gray to dark-yellos. The aggregate soil composition changes from tough muddy consistence to the cloddy one having a characteristic putrid odor. In 14 days the soil clods become incombustible; in 21 days no oil products are detected by chemical analysis, the microflore composition is regenerated. The decree of purification amounts virtually to 100%.

EXAMPLE 4

The water basin (one-hectare area) of an oil-stock yard contains 183 t of crude oil. Seven days after the basin has been treated with a suspension of the biomass of the bacterial culture of the strain of Arthrobacter species S-1212, containing 12 kg of the bone-dry biomass (the weight ratio between the biomass and the oil being $1:10^5$), the water surface develops bulges resulting from evolution of carbon dioxide gas. The oil film becomes consecutively brown, dark-red, light-orange, and then decomposes into rapidly disappearing fragments pierced by whitish aggregations of the microbial mass. In 20 days the film disappears (100% purification), water transparence is restored completely in 30 days.

EXAMPLE 5 a settling reservoir having 300 m$^2$ capacity is polluted with oil products (resinous substances, asphaltenes, crude oil) having a layer thickness of 1.0–1.5 cm, a total amount amount of the oil products being 558 kg. The settling reservoir is subjected to a single treatment with the paste of the biomass of the bacterial culture of the strain Acinetobacter special (bicoccum) B-6445. The paste contains 2.5 kg of the bone-dry biomass (the weight ratio between the biomass and the oil products being $1:10^3$), 5 kg of superphosphate, and 3 kg of ammonium sulfate. In 21 days the complete (100%) purification of the reservoir occurs.

EXAMPLES 6–11

600 ml of water polluted with crude oil is subjected to purification. The water is dispensed in 6 flasks by 100 ml each and 1 ml of crude oil is added to each of the flasks. The flasks are subjected to purification on a shaker. To this end, each of the flask is doped with nitrogen-and phosphorous-containing salts. Then added to the first flask is a water suspension of the strain of Acinetobacter species (biococcus) B-6445 (I), to the second flask, a water suspension of the biomass of the bacterial culture of the strain of Rhodococcus species S-1213 (II), to the third flask, a water suspension of the biomass of the bacterial culture of the strain of Arthrobacter species S-1212 (III), to the fourth flask, a water suspension of a mixture of the biomass of the bacterial culture of strains I and II, to the fifth flask, a water suspension of the biomass of the bacterial culture of a mixture of strains I and III, and to the sixth flask, a water suspension of the biomass of the bacterial culture of a mixture of strains I, II, and III. The weight ratio between the biomass being inoculated and the oil equals 1:10 in all Examples, respectively.

After 10 hours of constant stirring the degree of purification in the first flask is 15%, in the second flask, 13%, in the third flask, 12%, in the fourth flask, 70%, and in the fifth flask, 65%.

After 24 hours of constant stirring the degree of purification in all flasks is 100%.

INDUSTRIAL APPLICABILITY

The strains being proposed are featured by the hydrocarbon-oxidizing activity and may be used for environmental restoration of ecological conditions in the oil-producing, oil-processing, and some other industries. The proposed method can find widespread application in agriculture for land recultivation, restoration of purity of water basins and ponds, as well as in diverse branches of national economy concerned with the production, processing, handling, and application of oil and oil products.

I claim:

1. A method for microbiological treatment of various media and surfaces from petroleum pollution, said method comprising inoculating into the petroleum pollution at least one bacterial culture isolated from the biocenosis of active silt, containing the petroleum pollution, said culture incorporation the purified strain of Acinetobacter species (bioccum) B-6445, which was deposited on Jul. 6, 1993 in the All-Russian Collection of Industrial Microorganisms of the All-Russian Research Institute for Genetics and Selection of Microorganisms and representing an integrated trophic association, featuring a weight ratio between the biomass of said bacterial culture and the petroleum pollution being treated, equal to 1:10–10$^5$, respectively; and cultivating the Acinetobacter strain on said petroleum pollution, containing petroleum hydrocarbons, mineral salts of nitrogen and phosphorus, iron, manganese, potassium, magnesium, and sulfur, until destruction of the petroleum hydrocarbons being treated occurs, thus providing for cleaning from petroleum pollution.

2. A method according to claim 1, comprising cultivating said Acinetobacter strain on said petroleum pollution additionally containing the following microelements selected from the group consisting of iron, magnesium, manganese, and zinc.

3. A method according to claim 2, comprising cultivating said Acinetobacter strain on said petroleum pollution, containing the following ingredients 10 g/l o NH$_4$H$_2$PO$_4$, 10 g/l of KH$_2$PO$_4$, and 0.7 g/l of MgSO$_4$ 7H$_2$O.

4. A purified strain of Acinetobacter species (bicoccus) deposited on Jan. 19, 1993 in the All-Union Collection of Industrial Microorganisms at the All-Union Research Institute for Genetics and Selection of Microorganisms said strain having the following cultural-morphological characteristics:
cells on meta-infusion agar are immobile, appearing as short thick rods measuring 1.2–1.8, 1.5–3.4 m in a young culture, and having a coccal shape measuring 1.5 m in a three-day culture; the culture forms no spores; three-day colonies grown on meta-infusion agar are rounded in shape, with even edges, whitish in color, glossy, of the sour-cream consistency;

said strain having the following physiological-biochemical characteristics:
obligate aerobe, chemoorganotroph, catalase-positive, gram-negative, oxidase-negative, no demand for vitamins and additional growth factors; grows in a broad range of the culture medium pH values (3.8–8.5) and temperatures (10°–35° C.), utilizes mineral nitrogen and fixes atmospheric nitrogen;

said strain being non-pathogenic, non-toxic and having no hemolytic activity.

5. A method for microbiological treatment of various media and surfaces from petroleum pollution, said method comprising inoculating into the petroleum pollution at least one bacterial culture isolated from the biocenosis of active silt, containing the petroleum pollution, said culture incorporating the purified strain of Acinetobacter species (bioccum) B-6445, which was deposited on Jul. 6, 1993 in the All-Russian Collection of Industrial Microorganisms of the All-Russian Research Institute for Genetics and Selection of Microorganisms and representing an integrated trophic association, featuring a weight ratio between the biomass of said bacterial culture and the petroleum pollution being treated, equal to 1:10–10$^5$, respectively;

said strain being non-pathogenic, non-toxic, and having no hemolytic activity;

said strain being gram-negative;

said strain having the following cultural-morphological characteristics:
cells on meta-infusion agar are immobile, appearing as short thick rods measuring 1.2–1.8, 1.5–3.4 m in a young culture, and having a coccal shape measuring 1.5 m in a three-day culture; the culture forms no spores; three-day colonies grown on meta-infusion agar are rounded in shape, with even edges, whitish in color, glossy, of the sour-cream consistency;

said strain having the following physiological-biochemical characteristics:
obligate aerobe, chemoorganotroph, catalase-positive, gram-negative, oxidase-negative, no demand for vitamins and additional growth factors; grows in a broad range of the culture medium pH values (3.8–8.5) and temperatures (10°–35° C.), utilizes mineral nitrogen and fixes atmospheric nitrogen; and cultivating the Acinetobachter strain on said petroleum pollution, containing petroleum hydrocarbons, mineral salts of nitrogen and phosphorus, iron, manganese, potassium, magnesium, and sulfur, until destruction of the petroleum hydrocarbons being treated occurs, thus providing for cleaning from petroleum pollution.

* * * * *